United States Patent [19]

Yim

[11] Patent Number: 5,456,265
[45] Date of Patent: Oct. 10, 1995

[54] ENDOCERVICAL BRUSH ASSEMBLY AND METHOD FOR OBTAINING TISSUE SAMPLES

[76] Inventor: Duck S. Yim, 5250 N. Leamington Ave., Chicago, Ill. 60630

[21] Appl. No.: 127,786

[22] Filed: Sep. 28, 1993

[51] Int. Cl.⁶ .................................................. A61B 10/00
[52] U.S. Cl. .......................................................... 128/756
[58] Field of Search ................................... 128/749, 756, 128/757, 759

[56] References Cited

U.S. PATENT DOCUMENTS

| | | | |
|---|---|---|---|
| D. 316,488 | 4/1991 | Stormby | D4/131 |
| D. 317,361 | 6/1991 | Stormby | D24/141 |
| 3,776,219 | 12/1973 | Brown | 128/2 B |
| 3,877,464 | 4/1975 | Vemes | 128/759 |
| 3,881,464 | 5/1975 | Levene | 128/2 B |
| 4,078,656 | 3/1978 | Crane et al. | 206/223 |
| 4,108,162 | 8/1978 | Chikashige et al. | 128/2 B |
| 4,127,113 | 11/1978 | Nollan | 128/2 W |
| 4,227,537 | 10/1980 | Suciu et al. | 128/756 |
| 4,395,943 | 8/1983 | Brandli | 15/167 R |
| 4,586,604 | 5/1986 | Atter | 128/756 |
| 4,759,376 | 7/1988 | Stormby | 128/756 |
| 4,892,831 | 1/1990 | Wong | 128/759 |
| 5,191,899 | 3/1993 | Strickland et al. | 128/756 |
| 5,217,024 | 6/1993 | Dorsey et al. | 128/757 |
| 5,279,307 | 1/1994 | Mohajer | 128/757 |

FOREIGN PATENT DOCUMENTS 0653880  1/1986  Switzerland ............................ 128/757

*Primary Examiner*—Max Hindenburg
*Attorney, Agent, or Firm*—Olson & Hierl, Ltd.

[57] ABSTRACT

A brush assembly and method of using such brush assembly for obtaining endocervical tissue samples. The brush assembly includes a handle having an outer surface with a plurality of pointed edges and grooved portions disposed in an alternating manner about the outer surface and extending the length of the handle to facilitate manipulation and rotation of the handle during use without slippage. A brush is attached to one end of the handle for collecting tissue. A semi-hemispherical bead is attached to the end of the brush to prevent patient discomfort during insertion of the brush assembly into the vagina. A sleeve surrounding the brush assembly protects the brush from contamination by vaginal tissue during insertion and removal of the brush assembly. During insertion, the sleeve covers the brush. When the brush is in its desired sampling position, the sleeve is slid away from the brush to expose the brush. The handle is then manipulated and rotated one or more turns, as counted by a turn mark on the handle, to scrape tissue samples from the wall of the cervix opening. Once the sample has been collected, the sleeve is slid back over the brush, and the brush assembly is withdrawn from the vagina. In an alternate embodiment, the brush assembly is comprised of two interconnecting shafts.

12 Claims, 2 Drawing Sheets

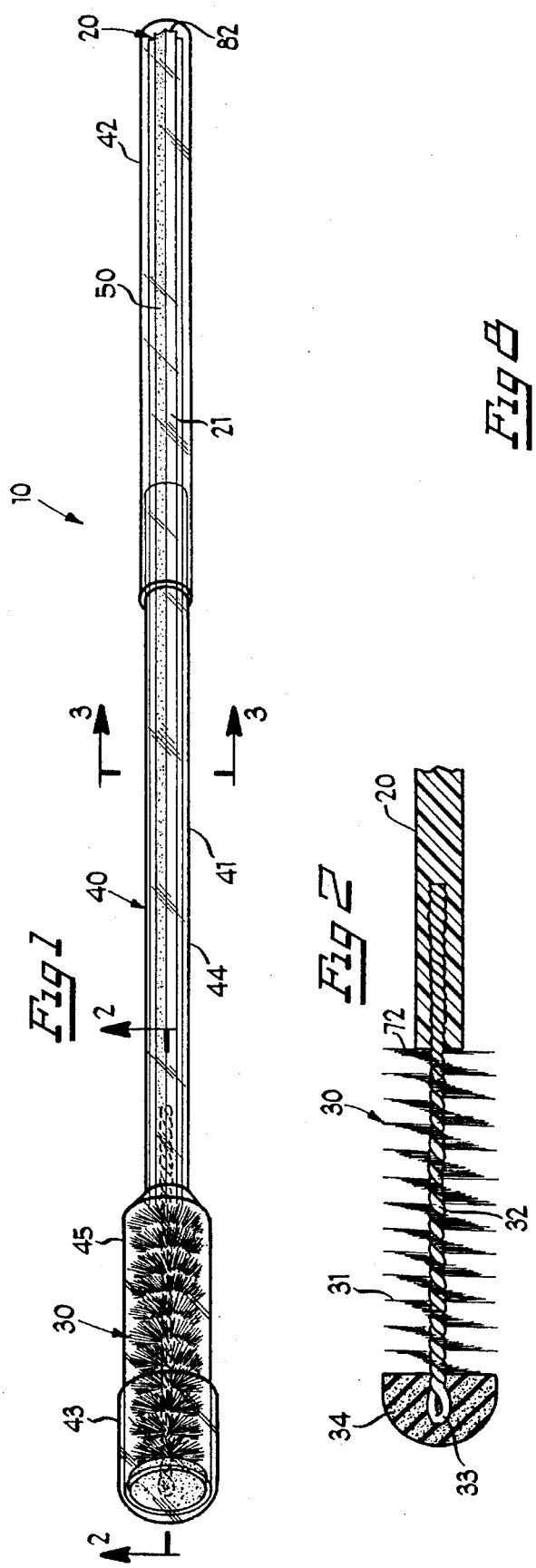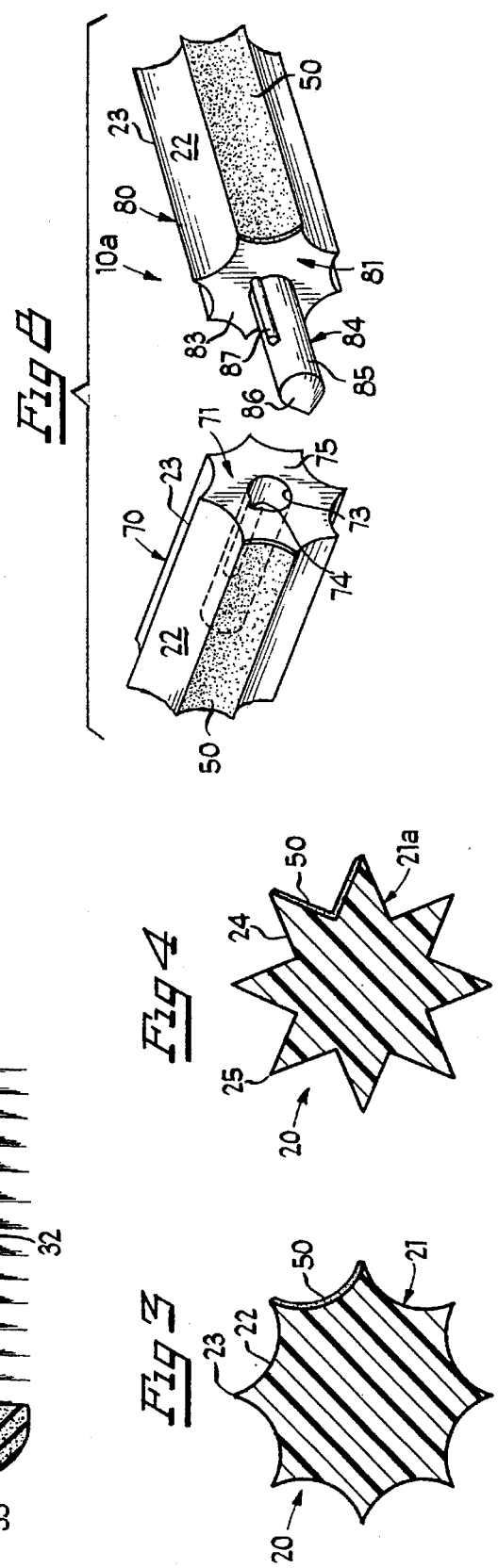

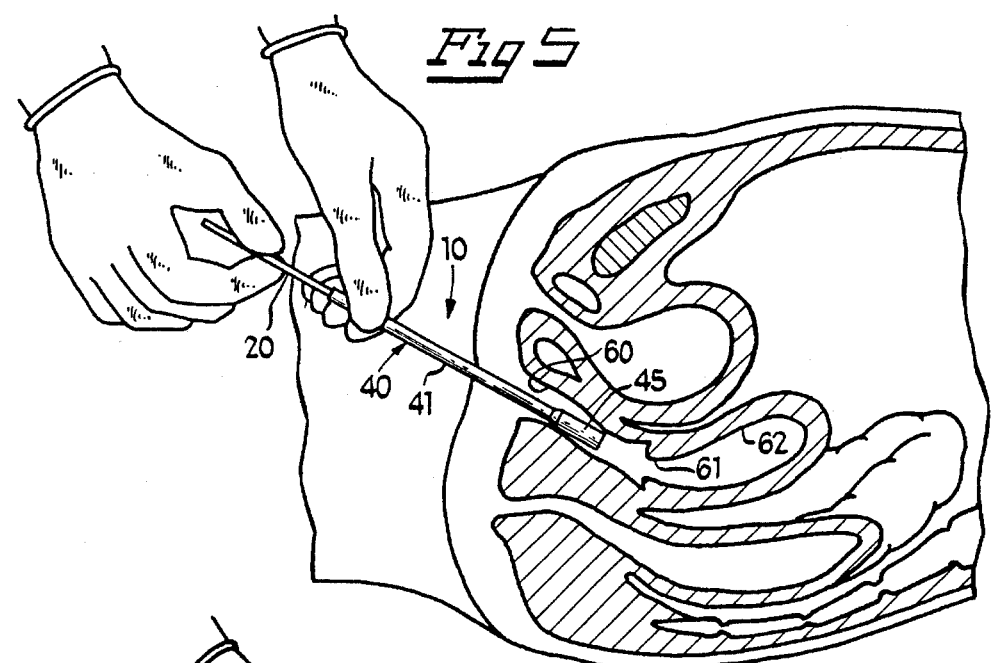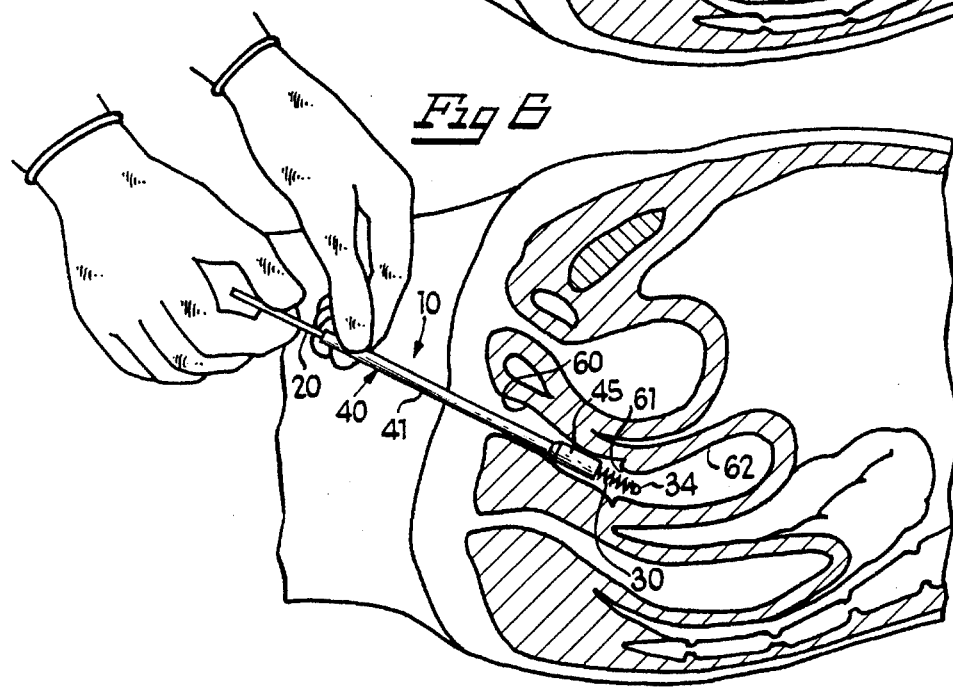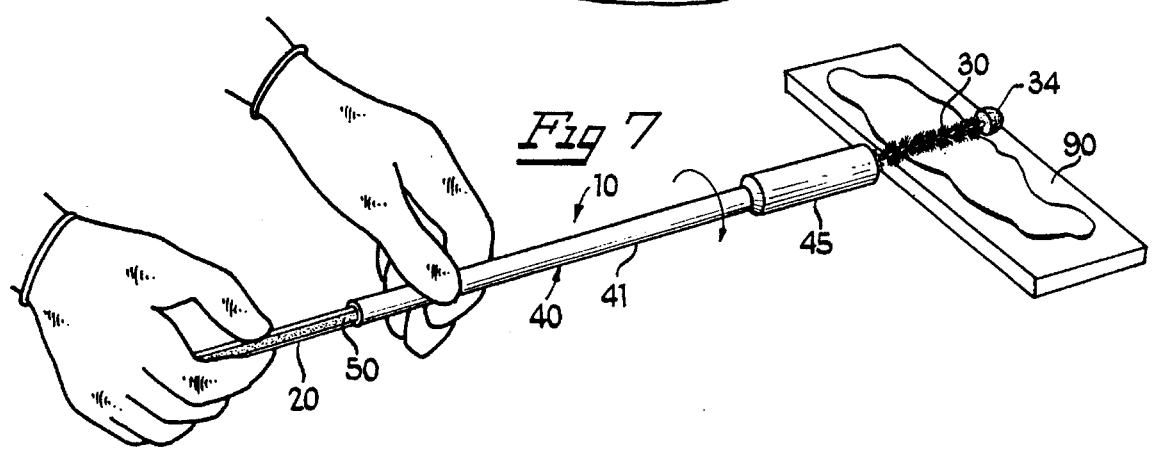

ENDOCERVICAL BRUSH ASSEMBLY AND METHOD FOR OBTAINING TISSUE SAMPLES

BACKGROUND OF THE INVENTION

The present invention relates to an improved brush assembly and method for obtaining endocervical tissue samples.

Since the introduction of cervical cytology screening by George Papanicolaou in 1940, the Papanicolaou smear has become a well-known procedure for the early detection of abnormalities of the cervical epithelium which has led to the reduction of mortality from carcinoma of the uterine cervix.

A number of devices have been developed to collect samples from the cervix. These devices have included: cotton swabs, applicators, wooden spatulas and endocervical sample collecting brushes. However, a broad range of false negative results from the Papanicolaou smear have been reported due, in part, to the sampling devices used and the method in which these devices have been used.

Although endocervical sample collecting brushes and endometrium sample collecting brushes are well known and popular among practitioners, there are many disadvantages associated with the present brushes. One of the disadvantages is that none have adequately addressed the need to protect health care workers from infection or transmission of the human immunodeficiency virus.

One of the commonly used brush assemblies is comprised of an elongated handle to which is attached a rectangular or cone-shaped brush head. During use, the brush assembly is inserted inside the vagina to place the brush at the opening of the endocervical canal and is then rotated one or more full turns to scrape off tissue material. Then the brush assembly is removed, and the tissue material is deposited onto a microscope slide for examination.

A disadvantage associated with this type of brush assembly is that its tip comprises a helically-wound, thin wire which extends beyond the bristles. Upon insertion into the vagina and endocervical canal, the tip may contact the walls of the vagina and endocervical canal. This contact causes patient discomfort and increases the risk of potential injury to the vagina and endocervical canal.

A second disadvantage is the shape of the handle which is generally cylindrical and typically includes a smooth outer surface. Since the user grasps the handle while wearing latex examination gloves dusted with corn starch, there is a tendency, due to the handle's cylindrical shape and smooth outer surface, for the user's thumb or finger to slip off the handle while the brush is manipulated and rotated during use.

As indicated above, the brush assembly is rotated one or more full turns when collecting tissue material and also when depositing the tissue onto the microscope slide glass for examination. Another disadvantage associated with available brush assemblies is the inability to accurately determine the number of times the brush has been turned.

Another disadvantage associated with this type of brush assembly is its size, and more particularly, the length of the handle. A typical brush assembly is approximately 17–20 cm in length and thus requires a package of approximately the same length. The need for such a lengthy package unnecessarily increases manufacturing costs and the amount of space which such a brush occupies in a doctor's or hospital's already crowded medical supply cabinet.

Yet another disadvantage associated with this type of brush assembly is the tendency of the brush to come into contact with the walls of the vagina and cervical canal, both during insertion and removal, thus contaminating the tissue sample collected from the cervix.

Yet another disadvantage associated with this type of brush assembly is that it requires the use of a speculum to enlarge the vaginal opening and allow insertion and removal of the brush assembly without contacting the walls of the vagina, thus preventing contamination of the brush with unwanted tissue. A disadvantage associated with the use of a speculum is patient discomfort during use thereof.

Yet another disadvantage associated with this type of brush assembly is that, following removal from its protective packaging, the brush is susceptible to contamination through handling and manipulation both prior to and during use, and further, is not adapted for aseptic disposal.

SUMMARY OF THE INVENTION

It is a general object of the present invention to provide a brush assembly and method for obtaining endocervical tissue samples which avoids the disadvantages of prior brush assemblies and methods while affording additional advantages.

An object is to provide a brush assembly which minimizes the risk of infection or transmission of the human immunodeficiency virus.

Another object is to provide a brush assembly where the risk of potential injury to the vagina and cervical canal and patient discomfort during insertion of the brush assembly are eliminated.

Another object is to provide a brush assembly where the handle may be manipulated and turned without the risk that it will slip off the user's thumb or fingers.

Yet another object is to provide a brush where the number of turns of the brush during use may be accurately counted.

Another object is to reduce the size of the packaging required for a brush assembly, thus reducing manufacturing costs and the space which such a brush occupies in a doctor's or hospital's medical supply cabinet.

Yet another object is to provide a brush assembly where risk of tissue sample contamination during insertion and removal is eliminated.

Yet another object is to provide a brush assembly which may be used without a speculum, thus eliminating patient discomfort resulting from the use thereof.

Yet another object is to provide a brush assembly which remains sterilized and uncontaminated both prior to and during use and which may be disposed of aseptically.

In summary, there is provided an endocervical brush assembly for obtaining tissue samples comprising an elongated handle adapted for grasping and turning by the fingers of a user, the handle including an outer lateral surface and opposed ends, the outer surface having a plurality of pointed edges and grooved portions disposed in an alternating manner about the outer surface and extending the length of the handle, the fingers of the user contacting a portion of the edges to facilitate the manipulation and rotation of the handle without slippage, an elongated brush attached to one of the ends of the handle for collecting endocervical tissue, the brush being comprised of a plurality of bristles supported by a wound wire shaft having an end thereof attached to one end of the handle.

Additionally, the brush assembly comprises a semi-hemispherical bead secured to the end of the wound wire shaft opposite the end thereof attached to the end of the handle.

Still further, the brush assembly comprises a sleeve which surrounds the brush assembly, the sleeve including an elongated member surrounding the handle and brush, and the sleeve further including first and second caps, the first cap surrounding one end of the handle and secured to one end of the member, the second cap surrounding the brush and secured to the other end of the member.

Additionally, the brush assembly comprises turn mark means on the outer surface of the handle for counting the number of turns of the brush during use.

Further, the method for using the brush assembly includes the steps of grasping the end of the handle adapted for grasping and turning, grasping the member of the sleeve such that the member remains over the brush, inserting the brush assembly into the vagina towards the cervix opening, sliding the member away to expose the brush, placing the brush in contact with the wall of the cervix opening, turning the end of the handle adapted for turning, thereby entrapping endocervical tissue in the bristles of the brush, sliding the member back over the brush such that the member surrounds the brush, removing the brush assembly from the vagina, sliding the member of the sleeve away to expose the brush, and separating the tissue from the bristles of the brush.

Additionally, in an alternate embodiment of the invention, the brush assembly comprises interconnecting shafts.

The invention consists of certain novel features and a combination of parts, hereinafter fully described, illustrated in the accompanying drawings and particularly pointed out in the appended claims, it being understood that various changes in the details may be made without departing from the spirit or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation and many of its advantages should be readily understood and appreciated.

FIG. 1 is a perspective view of a brush assembly constructed in accordance with the features of the present invention;

FIG. 2 is a partial, longitudinal, sectional view taken along the line 2—2 of FIG. 1 with the sleeve removed therefrom;

FIG. 3 is an enlarged, vertical, sectional view taken along the line 3—3 of FIG. 1;

FIG. 4 is a vertical, sectional view, similar to FIG. 3, depicting an alternate embodiment of the outer surface of the handle;

FIG. 5 illustrates the method of insertion of the brush assembly;

FIG. 6 illustrates the method of collection of a tissue sample;

FIG. 7 illustrates the method of rotation of the brush assembly to smear the collected tissue sample onto a microscope slide glass; and FIG. 8 is an enlarged, broken perspective view of an alternate embodiment of the brush assembly of the present invention.

DETAILED DESCRIPTION

Turning now to the drawings, and more particularly to FIG. 1, there is depicted a brush assembly, generally designated 10, constructed in accordance with the present invention. The brush assembly 10 comprises an elongated handle 20, a brush 30 and a sleeve 40.

Referring to FIG. 2, brush 30 is comprised of a plurality of bristles 31 supported on a wound wire shaft 32 which terminates in a loop 33. In the embodiment depicted, brush 30 is generally cylindrical in shape. A semi-hemispherical bead 34 is secured to the loop 33. The bead 34 is comprised of a sponge material such as a soft polymer.

Referring to FIGS. 1 and 3, handle 20 includes an outer, lateral surface 21 having a plurality of concave sides or portions 22 which define a plurality of peripheral, pointed edges 23 which are spaced around the outer surface 21 in an alternating manner and extend longitudinally along the length of handle 20. As addressed above, currently available brush assemblies typically include a handle with a flat, cylindrical, outer surface which is grasped by a user wearing latex examination gloves dusted with corn starch. The combination of the flat, cylindrical, outer surface and the use of corn-starch-covered gloves has made the task of manipulation and turning of the brush without slippage difficult. According to the present invention, handle 20 is adapted for grasping by the fingers of a user, as shown in FIGS. 5–7, without slippage. Brush assembly 10 is handled as shown in FIGS. 5 and 6 such that the thumb, index finger and middle finger engage a portion of edges 23 and concave portions 22, thus providing a firm grip on handle 20 and facilitating manipulation and turning of the handle without slippage.

FIG. 4 shows an alternate embodiment for the outer surface of handle 20 which also provides for a firm grip during use of handle 20. In this embodiment, outer surface 21a includes a plurality of longitudinally extending V-shaped grooves 24 which define a plurality of edges 25 which are spaced around outer surface 21a and extend longitudinally along the length of handle 20. According to the invention, the fingers of the user, and more particularly, the thumb, index finger and middle finger of the user, contact the grooves 24 and edges 25 to provide a firm grip and facilitate the manipulation and rotation of handle 20 without slippage.

Referring to FIGS. 1 and 3, handle 20 also includes a turn mark 50 comprising a strip of colored material which is placed on one of the sides 22, by painting or the like, to allow the user to accurately count the number of times brush assembly 10 has been rotated during collection of tissue material and also when depositing the tissue material onto a microscope slide glass for examination. In addition to a strip of colored material, turn mark 50 may alternatively be comprised of any type of identification mark imprinted onto one of the sides 22, such as the manufacturer's name or trademark. The turn mark 50 may also be placed on the outer surface 21a of handle 20, as depicted in FIG. 4.

Referring to FIG. 1, protective sleeve 40 includes a cylindrical elongated member 41, and telescopic cylindrical elongated caps 42 and 43. Member 41 has a first cylindrical portion 44 which surrounds handle 20. The diameter of portion 44 is slightly greater than the diameter of handle 20. Member 41 also has a second cylindrical portion 45, extending integrally from portion 44, which surrounds brush 30. Portion 45 has a diameter greater than portion 44 and brush 30. Cap 42, which has a diameter slightly greater than portion 44, surrounds the end of handle 20 and telescopes the end of portion 44, thus securing the same to portion 44. Cap 43, which has a diameter slightly greater than portion 45, surrounds brush 30 and telescopes portion 45, thus securing the same to portion 45. According to the invention, sleeve 40 is made of a clear plastic material and is filled with ethylene oxide to sterilize brush assembly 10.

In the present embodiment of the invention, handle 20 has an effective diameter of approximately 3 mm and is approximately 175 mm in length. Brush 30 is approximately 6 mm in diameter and 18 mm in length. These dimensions may be varied to suit different requirements.

During use, caps 42 and 43 are initially removed from the ends of member 41 of sleeve 40. Then brush assembly 10 is grasped by a user, as shown in FIG. 5, such that the thumb, index finger and middle finger of one hand grasp handle 20, and the thumb, index finger and middle finger of the other hand grasp member 41 of sleeve 40 such that the portion 45 thereof remains around brush 30 and bead 34. Thereafter, and as shown in FIG. 5, brush assembly 10 is slid into the vagina 60 towards the opening 61 of the cervix 62 with portion 45 still around brush 30 to prevent brush 30 from being contaminated with tissue from the walls of the vagina 60 during insertion. Bead 34 is semi-hemispherically shaped to prevent injury to surrounding tissue and to minimize patient discomfort which might result during insertion from contact with the walls of the vagina 60. The end of member 45 is also rounded to prevent injury to surrounding tissue and minimize patient discomfort during insertion. Then, and as shown in FIG. 6, the user slides member 41 of sleeve 40, and thus portion 45 thereof, away from brush 30. Brush 30 is then placed against the wall of the cervix opening 61 and is rotated one or more turns, as counted by turn mark 50 (FIGS. 1 and 3), to allow bristles 31 and bead 34 to entrap and collect tissue material. Upon completion of the collection of tissue, brush 30 is moved away from the wall of the cervix opening 61, and then member 41 of sleeve 40 and, more particularly, portion 45 thereof is slid back over brush 30. Brush assembly 10 is then removed from the vagina 60. Replacing member 41 over brush 30 prior to removal eliminates the risk of contamination of the tissue sample during removal with tissue from the vagina 60.

According to the invention, a Pap smear may be performed without the use of a speculum. A speculum is typically used to enlarge the vaginal opening to allow insertion and removal of the brush assembly without the brush contacting the walls of the vagina, thus preventing contamination of the brush with unwanted tissue. The pap smear may be performed without a speculum since member 41 of sleeve 40 and, more particularly member 45 thereof, covers brush 30 both during insertion and removal, thus serving the speculum's purposes of eliminating the risk of tissue contamination. The present brush assembly also eliminates patient discomfort resulting from the use of a speculum.

After removal, member 41 of sleeve 40 and, more particularly, member 45, is once again slid away from brush 30 to expose brush 30 and bead 34. Then, as shown in FIG. 7, the collected sample is separated from bristles 31 and bead 34 and deposited onto an examination microscope slide 90 by rotating brush 30 on the surface thereon one or more full turns, as counted by turn mark 50.

Then, member 41, and more particularly member 45, is slid back over brush 30, caps 42 and 43 are put back on the ends of sleeve 40 and the assembly brush 10 is disposed of.

Sleeve 40, which allows for the aseptic disposal of brush assembly 10, eliminates the risk of infection or transmission of viruses such as the human immunodeficiency virus which has resulted from the accidental and negligent handling and manipulation of medical waste.

In an alternate embodiment of the invention, the brush assembly 10 of FIG. 1 may comprise a handle 20, a brush 30, and a protective package such as a plastic wrap, instead of a sleeve 40. In this embodiment, the plastic wrap is completely removed just prior to use. The brush assembly 10 would be used to collect and examine tissue samples in the same manner as described above except that the method of insertion and removal would not include the steps required as a result of the use of sleeve 40.

FIG. 8 depicts another alternate embodiment of the brush assembly, generally designated 10a. In this embodiment, brush assembly 10a comprises first and second interconnecting shafts 70 and 80, respectively. Shaft 70 is generally cylindrical and includes an inner end 71 and an outer end 72 (FIG. 2). Inner end 71 has a cylindrical aperture 73 which extends centrally and longitudinally from end 71 through a portion of shaft 70. Aperture 73 also includes a groove 74. The inner end 71 is defined by a flat contact face 75 extending radially outwardly from aperture 73.

Shaft 80 is generally cylindrical and includes an inner end 81 and an outer end 82 (FIG. 1). Inner end 81 is defined by a flat contact face 83. A finger or tip 84, centrally disposed on face 83, extends longitudinally outwardly from the inner end 71. Finger 84 includes a cylindrical base portion 85 and a conical tip portion 86. Face 83 extends radially outwardly from the base of finger 84. Finger 84 also includes an ear 87 extending radially outwardly from the surface thereof. Finger 84 is integrally molded as part of shaft 80.

Shafts 70 and 80 are of equal effective diameter. Further, finger 84 and aperture 73 are of an equal diameter less than the effective diameter of shafts 70 and 80. According to the present invention, shafts 70 and 80 are interconnected by press-fitting finger 84 into aperture 73 such that ear 87 fits within groove 74 and until contact faces 75 and 83 contact and abut each other. The keying of ear 87 within groove 74 prevents the rotation of shafts 70 and 80 independently of each other during use. The use of interconnecting shafts 70 and 80 allows brush assembly 10a to be stored in a package half the size of current packages, thus reducing manufacturing costs and reducing by half the storage space required for such a brush assembly in a doctor's or hospital's already crowded medical supply room or cabinet.

In this alternate embodiment, shaft 70 is approximately 80 mm in length, and shaft 80 is approximately 95 mm in length. Finger 84 and aperture 73 are each approximately 1.2 mm in diameter. However, these dimensions may be varied to suit different requirements.

Brush assembly 10a is otherwise identical in structure to brush assembly 10 except that it does not include a protective sleeve 40. In use, brush 10a is initially removed from a protective package such as a plastic wrap, and shafts 70 and 80 are interconnected as explained previously. Brush assembly 10a is used to collect and examine tissue samples in the same manner as brush 10, as shown in FIGS. 5–7, except that the method of insertion and removal does not include the steps required as a result of the use of sleeve 40.

What is claimed is:

1. An endocervical brush assembly for obtaining tissue samples comprising:

an elongated handle adapted for grasping and turning by the fingers of a user, said handle including an outer circumferential surface and longitudinally opposed ends, said outer surface having a plurality of longitudinally and circumferential extending adjoining concavely grooved portions, each of said grooved portions including first and second opposed sides, each of said first and second sides of each said grooved portion being joined to a respective said first and second side of a different circumferentially adjoining grooved portion such that each such pair of joined sides forms a longitudinally and outwardly extending pointed edge portion, said grooved portions and said pointed edge portions being disposed in an alternating circumferential relationship about said outer surface, whereby said fingers contact and grasp said edge portions to facilitate the manipulation and rotation of said handle without slippage; and an elongated brush attached to and longitudinally extending outwardly from one of said ends of said handle for collecting endocervical tissue, said brush being comprised of a plurality of bristles supported by an elongated shaft having a rear end thereof attached to said one end of said handle.

2. The brush assembly of claim 1, wherein said shaft is comprised of spirally wound wire and wherein a semi-hemispherical tissue collecting bead is secured to the forward end of said wound wire opposite said rear end thereof, said bead having a diameter approximately equal to the diameter of said brush.

3. The brush assembly of claim 2, wherein said tissue collecting bead is composed of a sponge material.

4. The brush assembly of claim 1, further including a sleeve assembly which surrounds said brush assembly, said sleeve assembly comprising an elongated tubular member which circumferentially and longitudinally slidably surrounds said handle and said brush, and first and second end caps, said first end cap surrounding one end of said handle and being detachably secured to one end of said tubular member, said second end cap surrounding said brush and being detachably secured to said other end of said tubular member, whereby said end caps are completely detached and removed from said brush assembly prior to use of said brush assembly, 5. The brush assembly of claim 4, wherein said tubular member includes a first portion surrounding said handle and a second portion surrounding said brush, said first portion having a diameter greater than the diameter of said handle, said second portion having a diameter greater than said first portion and greater than the diameter of said brush, said first cap being detachably secured to said first portion, and said second cap being detachably secured to said second portion.

6. A method for obtaining endocervical tissue including the following steps:

providing a brush assembly comprising an elongated handle including opposite ends, one of said ends being adapted for grasping and turning by the fingers of a user, an elongated brush for collecting endocervical tissue, said brush being attached to the end of said handle opposite the end adapted for grasping and turning, a brush comprised of a plurality of bristles, and a sleeve surrounding a portion of said brush assembly, said sleeve including an elongated member surrounding a portion of said handle and brush;

grasping the end of said handle adapted for grasping and turning and not surrounded by said member of said sleeve;

grasping said member of said sleeve such that said member remains over said brush;

inserting said brush assembly into the vagina towards the cervix opening;

sliding said member of said sleeve away to expose said brush;

placing said brush in contact with the wall of the cervix opening;

turning the end of said handle adapted for turning, thereby entrapping endocervical tissue in said bristles of said brush;

sliding said member of said sleeve back over said brush such that said member surrounds said brush;

removing said brush assembly from the vagina;

sliding said member of said sleeve away to expose said brush; and separating the tissue from said bristles of said brush.

7. The method of claim 6, further comprising the steps of:

providing a sleeve further including first and second caps, said first cap surrounding the end of said handle adapted for grasping and turning and secured to one end of said member, said second cap surrounding said brush and secured to the other end of said member;

removing said first and second caps completely from said member prior to insertion of said brush assembly into the vagina;

replacing said first and second caps onto said member after removing said brush assembly from the vagina; and disposing of said brush assembly.

8. An endocervical brush assembly for obtaining tissue samples comprising:

an elongated handle adapted for manual grasping by a user, said handle including first and second shafts of equal diameter, each of said first and second shafts including an outer circumferential surface and longitudinally opposed inner and outer ends, each of said inner ends including a flat face, said outer surface of each of said shafts having a plurality of longitudinally and circumferentially extending adjoining concavely grooved portions, each of said grooved portions including first and second opposed sides, each of said first and second sides of each said grooved portion being joined to a respective said first and second side of a different circumferentially adjoining grooved portion such that each such pair of joined sides forms a longitudinally and outwardly extending pointed edge portion, said grooved portions and said pointed edge portions being disposed in an alternating circumferential relationship about said surface;

coupling means for interconnecting the respective inner ends of said first and second shafts including a finger integral with and extending from the inner end of said second shaft and an aperture extending into the inner end of said first shaft, said finger and said aperture having a diameter less than the diameter of said first and second shafts, said finger being press fit into said aperture, and said flat faces being placed in abutting relationship to interconnect said first and second shafts; and an elongated brush attached to the outer end of said first shaft for collecting tissue, said brush including a plurality of bristles supported by a wound wire shaft having an end thereof attached to said outer end of said first shaft.

9. The brush assembly of claim 8, wherein said finger includes an ear, and said aperture includes a groove, said ear fitting into said groove when said finger is press fit into said aperture to prevent independent rotation of said first and second shafts.

10. The brush assembly of claim 8, further comprising a semi-hemispherical tissue collecting bead secured to the forward end of said wound wire shaft opposite the end attached to said outer end of said first shaft, said bead having a diameter approximately equal to the diameter of said brush.

11. The brush assembly of claim 10, wherein said tissue collecting bead is composed of a sponge material.

12. An endocervical brush assembly for obtaining tissue samples comprising:

an elongated handle adapted for grasping and rotatable turning by the fingers of a user, said handle including a forward end and a rear end;

an elongated brush attached to the forward end of said handle for collecting endocervical tissue, said brush being comprised of a plurality of bristles supported by an elongated shaft having an end thereof attached to the forward end of said handle; and a sleeve assembly which surrounds said brush assembly, said sleeve assembly comprising an elongated tubular member which circumferentially and longitudinally slidably surrounds said handle and said brush, said tubular member including a first portion surrounding said handle and a second portion surrounding said brush, said first portion having a diameter greater than the diameter of said handle, said second portion having a diameter greater than said first portion and greater than the diameter of said brush, said sleeve assembly further comprising first and second end caps, said first end cap surrounding one end of said handle and being detachably secured to the end of said first portion of said tubular member, said second end cap surrounding said brush and being detachably secured to the end of said second portion of said tubular member, whereby said end caps are completely detached and removed from said tubular member prior to use of said brush assembly.

* * * * *